United States Patent [19]

Weldes

[11] 3,959,274

[45] May 25, 1976

[54] PREPARATION OF ALKALI METAL AND QUATERNARY NITROGEN DOUBLE SALTS OF SILICIC ACID

[75] Inventor: Helmut Hans Wilhelm Weldes, Havertown, Pa.

[73] Assignee: Philadelphia Quartz Company, Valley Forge, Pa.

[22] Filed: July 9, 1973

[21] Appl. No.: 377,690

Related U.S. Application Data

[63] Continuation of Ser. No. 776,242, Nov. 15, 1968, Pat. No. 3,769,309, which is a continuation of Ser. No. 614,027, Feb. 6, 1967, abandoned, which is a continuation of Ser. No. 500,328, Oct. 21, 1965, Pat. No. 3,383,386, which is a continuation of Ser. No. 50,877, Aug. 22, 1960, Pat. No. 3,239,549.

[52] U.S. Cl. ..................... 260/247.7 L; 260/268 R; 260/326.5 A
[51] Int. Cl.² .......................................... C07F 7/10
[58] Field of Search ................. 260/247.7 D, 268 R, 260/326.5 A, 246 B Primary Examiner—James A. Patten
Attorney, Agent, or Firm—Fred Philpitt; Ernest Posner

[57] ABSTRACT

Double silicate salts of alkali metals and quaternary nitrogen compounds are prepared by the reaction of (a) an alkylene oxide, (b) an amine, and (c) an alkali metal silicate.

4 Claims, No Drawings

PREPARATION OF ALKALI METAL AND QUATERNARY NITROGEN DOUBLE SALTS OF SILICIC ACID

CROSS REFERENCE

This is a continuation of application Ser. No. 776,242, now U.S. Pat. No. 3,769,309, filed Nov. 15, 1968, which is a continuation application of my prior application, Ser. No. 614,027 filed Feb. 6, 1967, now abandoned, which in turn is a continuation application of Ser. No. 500,328 filed Oct. 21, 1965, now U.S. Pat. No. 3,383,386, which in turn is a continuing application of my prior Ser. No. 50,877 filed Aug. 22, 1960, now U.S. Pat. No. 3,239,549, which prior applications are hereby incorporated by reference in the present case.

THE INVENTION

This invention broadly relates to a process for the production of crystalline quaternary nitrogen compounds having the general formula:

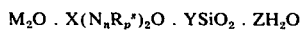

M preferably represents an alkali metal and most preferably sodium or potassium or mixtures thereof;

N represents a nitrogen atom;

n indicates the number of nitrogen atoms and is a small integer, less than 10 and preferably less than 5;

X, Y and Z represent numbers defining the relative amounts of each of the component parts of the compound. X is preferably between 0.5 and 1.5, Y is preferably between 2 and 10, and Z is preferably between 1 and 40, and wherein up to four R groups are associated with each N;

R represents an organic radical that forms with N an NR base selected from the group consisting of alkylamines, alkanolamines, heterocyclic amines and cyclic amines which produce solutions with a pH of at least 9;

p is equal to the number of R groups and is at least 4 and up to 4n;

s is an integer from 1 to p, indicating number of different types of R groups.

According to one specific embodiment the invention relates to a process for the production of compounds having the formula:

Wherein M, N, X, Y and Z have the significances noted above and $R^1$, $R^2$, $R^3$ and $R^4$ represent alkyl radicals containing between about 1 to 20 carbon atoms. Here p is 4 and s is 4 but may be any number from 1 to 4 inclusive.

In general, it can be said that the compounds of this invention are derived from nitrogen bases with a dissociation constant greater than that of $NH_3$ ($K = 1.8^{x10-5}$; pk = 4.74) and/or nitrogen bases which produce solutions with a pH of at least 9.

In accordance with the process of this invention, an alkylene oxide, e.g. ethylene oxide, is reacted with amines which in the presence of an alkali metal silicate will form quaternary ammonium ions corresponding to quaternary ammonium hydroxides, e.g. tetraethanolammonium hydroxide, tetrakis-2-hydroxyethyl piperazinium hydroxide, N, N'-bis-beta-hydroxyethyl morpholinium hydroxide, N, N,N'-tris-(beta-hydroxyethyl)-N'-[tris-(beta-hydroxyethyl)-ethylammonium]-piperazinium hydroxide. The alkali metal silicate acts both as catalyst and reactant to form the double salt. Any soluble alkali metal silicate may be employed.

The products of the reaction have been shown to be substantially independent of the $SiO_2/Na_2O$ ratio of the soluble silicate used in the preparation. For instance, in the reaction between sodium silicate solutions, ethanolamine, and ethylene oxide, crystals were prepared using sodium silicate solutions varying in percent by weight ratio of $SiO_2/Na_2O$ from 2.0 to 3.75. The final product varied in mol ratio over the following range: 1.0 $Na_2O$:1.0–1.5 $N^+(C_2H_4OH)_4$:3.0–3.8 $SiO_2$: 7.9–14.4 $H_2O$ (1$Na_2O$: 0.5–0.75($N(C_2H_4OH)_4)_2O$:0:3–3.8 $SiO_2$: 7.9–14.4 $H_2O$). It will be noted that the formulas have been shown in both the quaternary ammonium ion form and the equivalent quaternary ammonium oxide form with the ions shown by the cationic symbol ($^+$). For each mole of quaternary ammonium oxide there are two moles of quaternary ammonium cation. In some of these starting mixtures, potassium silicate was added to the sodium silicate without any essential change in the final product except that the alkali metal present was a mixture of sodium and potassium.

The reaction temperature has been varied from 25°C. to 150°C. but satisfactory products generally were not obtained at temperatures above about 100°C. Reaction time has been varied from 2 to 20 hours with some tendency for a lower ratio of the quaternary ion in the final product at the longer time limit.

For somewhat more complex derivatives I may react an alkylene oxide, such as ethylene oxide, with various amine compounds, whether primary, secondary or tertiary (such as triethanolamine, tetrahydroxyethyl ethylene diamine, ethylamine, monoisopropanolamine, morpholine, various piperazine compounds, and various pyrrolidine compounds) and at the same time or subsequently reacting with an alkali metal silicate as a catalyst and/or reactant.

In the preparation of alkali metal tetraalkanolammonium silicates, the following general rules are found to be important:

1. The amount of alkali metal silicate should not be too high in the reaction mixture. If it is increased above a reasonable upper limit, there is danger of gel formation and crystallization is slow. The isolation of the crystals becomes difficult because of the high viscosity of the mother liquor.

2. The amount of water distilled off from the final reaction mixture is quite critical.

3. The reaction temperature should be as low as possible, preferably room temperature or possibly lower. However, at temperatures much below room temperature, reaction time becomes unreasonably long.

4. Small amounts of potassium salts increase the speed of crystallization considerably.

5. The final solution supersaturates readily and therefore should be seeded and mechanical aids used for faster crystallization.

6. Some soluble silica appears to be necessary as a catalyst for the final step of the reaction to the quaternary form.

The ratio of silica to the combined alkali in the precipitated product can be increased by adding finely divided hydrated silica to the mixture. By this means the ratio of the $SiO_2$ in the precipitate has been raised from about 3.3 up to 9 or even higher on the mol basis (i.e. 6.6 to 18 $SiO_2$: quaternary ammonium oxide). Mixtures of tetraethanolammonium hydroxide and alkali metal oxide in silicate solutions are also possible by these procedures: For instance, a solution formed by mixing S-35 sodium silicate with a solution of sodium tetraethanolammonium silicate will have an $SiO_2:Na_2O$ ratio higher than that of S-35.

It should be noted here too that it is intended to include the intermediate solutions as part of this invention. They are used not only as a source of the quaternary ammonium silicate crystals, but may themselves be used in many of the same applications that will be described later. It is of particular importance that they represent solutions which may be raised to a very high ratio of silica to inorganic alkali and they may be concentrated to a rather high solids content. For instance, the following table shows Stormer viscosity in centipoises (Cp) at 20° C.

| Sodium Tetraethanol-ammonium Silicate | Solids Content | Cp |
|---|---|---|
| 63% by weight | 46.1% by weight | 48 |
| 59 | 43.2 | 29 |
| 56 | 41.0 | 20 |
| 53 | 38.8 | 14 |

These aqueous solutions also readily dissolve finely divided silica, such as Baker's analyzed silicic acid, a hydrated xerogel, or Quso (sold by Philadelphia Quartz Company) which is a hydrated precipitated silica, or Syloid-308 which is a finely divided silica gel sold by Davison Chemical Co., or Hi-Sil X-303 which is a hydrated precipitated silica sold by Columbia-Southern Chemical Co. These all may be dissolved in the above solutions at room temperature (See Example 2). It was found that silica from silica gel dissolved in my sodium quaternary ammonium silicates is in a completely crystalloidal state, whereas such silica dissolved in a normal sodium silicate, such as "N" silicate, is in a completely colloidal state. The difference was demonstrated by the reaction with ammonium molybdate solution which with crystalloidal silica in my solution develops a yellow color whereas no color was found in the sodium silicate solution.

The reaction system for the preparation of these quaternary ammonium silicates involves a number of variables. First, there is the amine, ethylene oxide, an alkali silicate and water. In addition, the effects of temperature and time are important. Thus, I have found that because of the high solubility of most of these quaternary ammonium alkali metal silicate compounds, the solutions need to be concentrated a great deal to induce crystallization. Secondly, as indicated above, I have found that lower temperatures tend to promote the proper reaction and, in general, I propose to use temperatures below 100° C. and preferably about room temperature, although with some reactants it is necessary to carry out the preliminary steps at a higher temperature and in an autoclave. The effects of these variables have been outlined in general terms above and become more apparent in the following examples. It is to be noted also that the alkali metal silicate has a catalytic effect on the crystallization of the product and mixed alkali silicates seem to be even more effective as seen by the addition of small amounts of potassium silicate to reactions involving sodium silicate primarily.

The concentration of alkali metal silicate is also of great importance. Where a high concentration is present, the speed of crystallization is greatly reduced. Thus, when sufficient sodium silicate is present to bring about complete reaction of the ammonium compound, crystallization is quite slow. On the other hand, if rapid crystallization is to be attained, the concentration of the sodium silicate may be only 50% of that necessary for the complete reaction with the quaternary ammonium ion. The presence of a small amount of potassium silicate is helpful with these sodium silicate solutions when the maximum yield is desired.

PROPERTIES OF ALKALI METAL TETRAETHANOLAMMONIUM SILICATE CRYSTALS

This crystalline compound has the approximate ratio of $1M_2O:1.4N^+(C_2H_4OH)_4:3.8SiO_2:11\ H_2O$ ($1M_2O:0.7(N(C_2H_4OH)_4)_2O: 3.8SiO_2:11H_2O$). It crystallizes from water in pseudo-cubic crystals which are either monoclinic or triclinic in crystal character. They are anisotropic and thus birefringent and they are either uniaxial or biaxial. Their refractive indices were found to be alpha = 1.498, beta = 1.506, and gamma = 1.528.

The crystals have a density at 20°/20° of 1.604 and a melting point of 57°–59° C. Softening begins at about 53° C. Solubility in water was found to be about 180 gms. in 100 ml of water at 20° C. and 35.5 gms. in 100 ml of water at 1.0° C. The crystals seem to be insoluble in all organic solvents. As indicated, the solubility rises rapidly as the temperature rises. Electrometric titration shows that this compound is a salt of a monobasic acid. It is either a double silicate salt or, if all the cationic groups can be combined as $R_2O$, the ratio appears to be $1R_2O:2.1-2.2SiO_2:7H_2O$ and the salt would be considered a disilicate. In the generalized formula $p$ equals 4, $s$ equals 1, $n$ equals 1.

A second crystalline product has the ratio of $1M_2O:0.6\ N^+(C_2H_4OH)_4:3.3SiO_2:8H_2O$ ($1M_2O:0.3(N(C_2H_4OH)_4)_2O:3.3SiO_2:8H_2O$). It has a crystalline habit similar to the above-described silicate but a melting point at about 82°–83° C. with softening beginning at 57° C. These crystals are also very soluble in water. When the cations are combined, the ratio appears to be $1R_2O:2.5SiO_2:6H_2O$.

EXAMPLES

A number of the materials used in the following examples are described as follows:

The alkali metal silicates, supplied by the Philadelphia Quartz Co., are:

| Trademark | Ratio $ZNa_2O:\%SiO_2$ | $Na_2O$ % | $H_2O$ % |
|---|---|---|---|
| S 35 | 1:3.75 | 6.75 | 67.9 |
| E | 1:3.22 | 8.60 | 63.6 |
| D | 1:2.00 | 14.70 | 55.8 |
| | %$K_2O:\%SiO_2$) | ($K_2O$) | |
| Kasil No. 1 | 1:2.50 | 8.30 | 70.5 |

Quso FF, a finely divided silica, also obtained as a trademarked produced from the Philadelphia Quartz Company, has an ignited loss of 13.0%, with 7.2% of free water and 5.8% of bound water. It analyzed approximately 85% $SiO_2$, with a surface area of about 280 $m^2/g$.

Another form of silica was Syloid-308 supplied by the trademark owner Davison Chemical Company. This silica had an ignited loss of 4.0 and contained approximately 95% $SiO_2$, with a surface area of about 230 $m^2/g$.

A finely divided silica Hi-Sil X-303, supplied by the trademark owner Columbia-Southern Chemical Company, had an ignited loss of 8.5% and contained approximately 89.4% $SiO_2$, with a surface area of about 140 $m^2/g$.

The ethylene oxide with a purity of about 99.5% was supplied by Matheson Company, Inc.

Ethanolamines were supplied by the Union Carbide Chemicals Co. as pure liquids. These were monoethanolamine ($H_2NC_2H_4OH$), diethanolamine $HN(C_2H_4OH)_2$, triethanolamine $N(C_2H_4OH)_3$.

Technical tetrahydroxy ethyl ethylene diamine was obtained from Visco Products Co.

Morpholine and propylene oxide came from Eastman Kodak Co. as 100% active liquid.

ANALYTICAL PROCEDURES

In analyzing the alkali quaternary ammonium silicates, the special procedures set foth in U.S. Pat. No. 3,239,549 were used and are incorporated herein by reference.

EXAMPLE 1

A series of experiments set out in Table I was carried out with 60 parts of triethaolamine using 21 parts of ethylene oxide in a closed autoclave at about 90° C. and 40 parts ethylene oxide in an open autoclave at the lower temperatures. Specifically the triethanolamine and ethylene oxide were first dissolved in water and then the E sodium silice was added with good agitation. A clear solution was obtained. This was placed in an autoclave and heated at 80° C. for about 5 hours. No pressure developed. A clear, yellowish solution was obtained, and water was distilled from this solution at 40° C. bath temperature and a reduced pressure of 25 to 30 mm Hg into an ice-cooled receiver. After about 55% of the water had been removed, the solution was clear and showed no signs of coacervation. A solution of this concentration containing triethanolamine and sodium silicate always coacervates. The solution was therefore placed in a refrigerator and seeded with quaternary ammonium silicate crystals. Within a few hours the crystals started to form and were filtered off after several days, washed with alcohol, ether and dried in a vacuum. The analysis of the crystalline product and the yield is shown in Table I. When the mother liquor was diluted with 1 part of ethanol to 7 parts of the liquor and placed back in the refrigerator, additional crystals were obtained.

TABLE I

Na-TEA silicates with a Ratio of $M_2O:N^+(C_2H_4OH)_4:SiO_2:H_2O::1:1.4:3.8:11$

| Reaction No. | Composition of starting mixture in parts by wt. | | | Reaction Temp. °C. | Reaction Time Hrs. | Yield | | Analysis — % by wt. | | | | |
|---|---|---|---|---|---|---|---|---|---|---|---|---|
| | "E" | "Kasil" No. 1 | $H_2O$ | | | % based on $SiO_2$ | % based on E.O. or amine | % Quat* | % $H_2O$ | % $SiO_2$ | % $Na_2O$ | % $K_2O$ |
| 1 | 120 | — | 320 | 90 | 5 | 12.4 | 6.2 | 35.82 | 25.11 | 30.65 | 8.24 | — |
| 2 | 120 | — | 320 | 90 | 2 | 26.5 | 12.7 | 33.17 | 29.02 | 29.49 | 8.12 | — |
| 3 | 228 | 16 | 300 | 70 | 20 | 24.9 | — | — | — | 31.33 | — | — |
| 4 | 228 | 16 | 300 | 25–30 | 19 | 31.8 | 29.2 | 32.67 | 28.84 | 29.50 | 8.32 | 0.28 |

Molar Ratio of $Na_2O+K_2O = 1$

| | CUZ,5-/25 Quat* | $SiO_2$ | $H_2O$ | Quaternary oxide |
|---|---|---|---|---|
| 1 | 1.4 : | 3.8 : | 10.5 | 0.7 |
| 2 | 1.3 : | 3.8 : | 12.3 | 0.65 |
| 3 | — | — | — | — |
| 4 | 1.2 : | 3.6 : | 11.7 | 0.6 |

*Quat = quaternary

The same process was carried out for reaction No. 2 in which the reaction time was only 2 hours.

A similar reaction was carried out using S-35 and D sodium silicate instead of E and crystallized tetraethanolammonium silicates were obtained.

In reaction No. 3 the mixture of E sodium silicate, KASIL No. 1, potassium silicate, water, triethanolamine and ethylene oxide was heated for 20 hours at 70° in an autoclave. The reaction product was a clear, colorless, odorless solution. After the 97% of the additional water was removed, the solution was refrigerated and within a day a large amount of crystals had formed. These were treated as before.

In reaction No. 4 the same mass was stirred in an open autoclave for 19 hours at room temperature. Again, the product was clear, colorless, and odorless, and after 97% of the water had been evaporated the solution was again refrigerated and the crystals separated and treated as before. At room temperature the yield was much higher than at the higher temperature.

EXAMPLE 2

The solutions of sodium tetraethanolammonium silicate readily dissolve silicic acid in the form of hydrated silicas such as those already described.

For example, 50 parts sodium tetraethanolammonium silicate were dissolved in 50 parts of water forming a solution of 34.2% solids content. When 24 parts silicic acid of the Baker's analyzed type, for instance, were placed in the solution and revolved on a ball mill, most of the silica dissolved and the mixture set to a jelly-like material. 30 parts additional of water were added and ball-milling continued. After 5 additional hours the mixture was filtered and the solution was found to have a composition of 2.26% $Na_2O$, 9.71% quaternary ions, 19.27% $SiO_2$; the mol ratio was $1Na_2O:1.4$ $N^+(C_2H_4OH)_4:8.8$ $SiO_2$ ($1Na_2O:0.7(N(C_2H_4OH)_4)_2O:8.8SiO_2$).

A similar solution was made up by dissolving completely 14 parts of the silicic acid. This had a mol ratio of $1Na_2O:1.4$ quaternary ion and 7 $SiO_2$ ($1Na_2O:0.7$ quaternary ammonium oxide:$7SiO_2$). The solution had a solids content of 40.34%.

A solution of 80 parts of sodium tetraethanolammonium silicate was dissolved in 50 parts of water containing 17.0% $SiO_2$ resulting in a ratio of 1 $Na_2O:1.4$ quaternary ion:3.8 $SiO_2$ ($1Na_2O:0.7$ quaternary oxide:$3.85SiO_2$). Sufficient finely divided Quso FF silica was added to give a final ratio of $Na_2O:SiO_2$ of 1:4.2. After 5.5 hours on the ball mill at room temperature all of the Baker's silicic acid and the Quso had dissolved. When using Syloid-308 or Hi-Sil X-303 in place of Quso in other runs, it was necessary to continue a ball milling overnight. Each of these solutions was clear and found to have a ratio of $1Na_2O:1.4$ quaternary ion:4.3 $SiO_2$ ($1Na_2O:0.7$ quaternary ammonium oxide:4.-$3SiO_2$).

The solutions were placed in a refrigerator for 6 days at 2° C. The well-crystallized precipitates were then isolated by filtration and washing with alcohol and ether and drying in vacuo as usual. The final product had a ratio of $1Na_2O:1.5$ quaternary ion:$4.2SiO_2:7.5$-$H_2O$ ($1Na_2O:0.75$ quaternary ammonium oxide:$4.2SiO_2:7.5H_2O$).

Similar reaction mixtures have been prepared and the product formed by spray drying the solution instead of allowing it to crystallize in a cake. In this way, the necessity of grinding the cake was avoided.

In one such case the amount of dilution water was sharply reduced to 60 parts in the formula given above. The preparation and crystallization of this mixture was carried out satisfactorily and the mass was spray dried using a ring type nozzle with six openings around the center, placed at the top of a 3 foot-2 inch conventional spray dryer. (A fluid atomizing research type spray dryer from the Swenson Corp. of Harvey, Ill. Best results were obtained with an air inlet temperature of 420°–430° C. and an outlet temperature of 80°–90° C. The atomizing air pressure was 75 psi and the slurry pressure was 50 psi. 69 Parts of product were obtained having the formula $1M_2O:1.3$ tetraethanolammonium ion:$3.9SiO_2:3.3H_2O$ ($1M_2$ $O:0.65$ tetraethanolammonium oxide:$3.9SiO_2:3.3H_2O$). The lower water content is probably related to the higher melting point which was found to be 108° C. The product decomposed at 173° C.

EXAMPLE 3

A high ratio solution was formed by first dissolving 50 parts of sodium tetraethanolammonium silicate of the normal type having a ratio of 1:1.5:4.0;13.3 ($1Na_2O:0.75$ quaternary ammonium oxide:$4.0SiO_2:13.3H_2O$) in 50 parts water. This dissolved completely. Then 20.7 parts of finely divided silica (Quso) were added and mixed on the ball mill for 36 hours at room temperature. A small amount of undissolved residue was centrifuged off and the solution was concentrated to a viscosity of about 2 poises by removing the water in vacuo at 40° C.

The final solution had a mol ratio of $1Na_2O:1.5N^+$ $(C_2H_4OH)_4:8.8SiO_2$ ($1Na_2O:0.75$ quaternary ammonium oxide: 24 $SiO_2$) and contained 67.1% $H_2O$. The Stormer viscosity at 20° C. was 62.7 sec.

EXAMPLE 4

The methods of preparing tetraethanolammonium hydroxide which involve the preparation of a salt and its subsequent reaction with barium or silver or similar hydroxide to form an insoluble residue which can be separated from the final organic hydroxide are known. It is possible to prepare a pure tetraethanolammonium hydroxide directly from ammonia and ethylene oxide using an alkali silicate or soluble silica as a catalyst. Thus, a mixture of 10 parts of E sodium silicate as catalyst was made with 300 parts of water and 24 parts of concentrated ammonium hydroxide solution containing 29% $NH_3$. These were mixed in an open flask with a reflux condenser and the reaction was allowed to proceed at its own rate with the ethylene oxide added gradually to the reaction mixture at room temperature. The temperature at the start was 24° C. and the solution was clear. In six minutes at 25° C., the ethylene oxide had also warmed up to 25° C. and was being added slowly. Two minutes later, the temperature rose to 27° without any refluxing occurring. At nine minutes, the temperature was 28° C. and although no refluxing was occurring, the reaction mixture was kept cool by cooling the outside of the flask. At 12 minutes, the temperature was still 28° C. At 17 minutes, the temperature had risen a half a degree and the mixture was refluxing very slowly. At 46 minutes, the temperature was 28° C. and all the ethylene oxide had gone over into the mixture which was clear. At 72 minutes refluxing had stopped but the temperature was the same. After 6.25 hours, the temperature was 26° C. and the reaction had stopped. There was still odor of ammonia, but neither ammonia nor ethylene oxide could be detected the next morning. The solution was then distilled in a vacuum of 16 mm of mercury until 312 parts of water was lost and distillation was continued at about three mm Hg with a loss of 2.3 parts of water. The remaining 92 parts were a clear and highly viscous solution. Four hundred and forty parts by volume of methanol were added and mixed in well and left over the weekend. Precipitated material was filtered off and the solution was made up to 500 parts by volume with methanol and titrated electrometrically. The clear and highly viscous oil was found to consist of about 41% of tetraethanolammonium hydroxide and 28% of triethanolamine. It is thus possible to prepare a pure tetraethanolammonium hydroxide quite cheaply in this manner by removing the amine and the solution will dissolve silica with the preparation of tetraethanolammonium silicate if desired.

EXAMPLE 5

A number of quaternary ammonium compounds more complex than the tetraethanolammonium hydroxide may be used to react with dispersions of silica gel or solutions of soluble alkali silicate to form complex organic silicates in which all of the sodium is displaced. It is possible, for instance, to use 150 parts E silicate, 300 parts water, and 60 parts of tetrahydroxy ethyl ethylenediamine in solution. The clear solution obtained from this mixture was poured into a vessel equipped with a stirrer, a thermometer, a gas inlet tube, and a low temperature reflux condenser. 23 Parts of ethylene oxide was added slowly through the gas inlet tube while the mixture was stirred vigorously. The exothermic reaction made it necessary to cool the reaction vessel to hold the temperature between 25° and 30° C.

to obtain the maximum yield. After 12 minutes the temperature was 28° C., no refluxing was occurring but the vessel was cooled. After 24 minutes the temperature was still 27° C. and the solution was somewhat more hazy. By 30 minutes all of the ethylene oxide had passed over and the temperature was 26° C. The solution was clear in 2.5 hours, and at 6 hours 14 minutes the temperature was still 25.5° C. with no odor of ethylene oxide. Ninety-six percent of the 300 parts water were distilled away leaving a viscous turbid solution which separated into two layers when left in the refrigerator at 2° C. Thirty parts water were added again which allowed the mixture to form a homogeneous solution and on refrigeration cube-like crystals of sodium hexahydroxyethyl ethylene diammonium silicate formed slowly.

EXAMPLE 6

It is evident that this reaction can be carried out with ethylene oxide and any of the other water miscible amines. For instance, in one reaction 140 parts of E sodium silicate was diluted with 300 parts of water and 10 parts ethylamine was added. Thirty-two parts of ethylene oxide was allowed to run into the reaction flask with the temperature controlled as usual. It was noteworthy that during this reaction no coacervate formed and when the reaction was complete, 295 parts of water was distilled off. It was found that on cooling, two layers appeared and it was necessary to return 20 parts of water to the solution, after which crystals formed slowly on standing.

EXAMPLE 7

Monoisopropanolamine will react with ethylene oxide in this reaction. For instance, a mixture of 30 parts of monoisopropanolamine was dissolved in 300 parts of water and 228 parts of E sodium silicate. To this was added 16 parts of Kasil No. 1 potassium silicate and the reaction was carried out as before in the flask at about 25°–30° C. The 53 parts of ethylene oxide were added slowly with cooling of the reaction mixture. No refluxing occurred, but after about ½ hour, a heavy coacervate formed. The ethylene oxide was added in the course of about 1 hour and in about 6 hours all the coacervate had dissolved. No ethylene oxide odor could be detected after standing overnight and then 189 parts of water were distilled off, leaving a clear solution. It was necessary to return 20 parts of water to maintain a single homogeneous solution in the refrigerator at 2° C.

Similarly, a solution may be formed by the reaction between propylene oxide and triisopropanolamine. In this case, 76.5 parts of triisopropanolamine were mixed with 600 parts of water and 120 parts of E sodium silicate, forming a clear solution to which the propylene oxide was added drop-wise at room temperature. A large amount of coacervate formed in the mixture overnight and it was necessary to continue the reaction much longer since the propylene oxide could still be detected.

EXAMPLE 8

A sodium-N,N-bis-beta-hydroxyethylmorpholinium silicate may be formed by the reaction of ethylene oxide with morpholine. In the presence of the alkali silicate, the ethylene oxide adds to the imine group forming two ethanol side chains. This is a tetraethanolammonium hydroxide in which two OH groups have condensed with the loss of water, forming a morpholine ring.

In this case, 114 parts of E sodium silicate were mixed with 8 parts of Kasil No. 1 potassium silicate in 300 parts of water and 35 parts of morpholine. This formed a clear solution and reaction started at 24° C. Cooling was started after 9 minutes when the temperature reached 28° C. and coacervation started at about 14 minutes and 30° C. In 35 minutes, all of the ethylene oxide had been passed into the solution and the temperature was 26.5° C. No refluxing occurred during this time. In 5.75 hours, the temperature was 23° C. The solution was clear. All coacervate had dissolved and there was no remaining odor of ethylene oxide.

Two hundred and seventy parts of water were distilled off to the point at which the reaction mixture became cloudy. This mixture separated into two layers on cooling, but in 2 days crystals started to form at the interface between layers and the mixture was accordingly stirred in an ice bath for seven hours. Thus, a large amount of crystals formed which were filtered off and washed and dried as usual, using ethanol and ether and a vacuum drier. The yield was 27% based on silica and 14% based on the ethylene oxide or morpholine.

This product had the molar ratio of $1(Na_2O+K_2O):1.15$ morpholine complex:$3.23SiO_2$:$12.1H_2O$($1$-$M_2O$:$0.58$ morpholine complex oxide:$3.23SiO_2$:$12.1$-$H_2O$). The crystals were semi-cubic and had the indices of refraction alpha=1.494, beta=1.498 and gamma=1.502. The recrystallized product melted at 62°–64° C. but began to soften at about 55° C. It was quite soluble in water, but not in the usual organic solvents.

EXAMPLE 9

A sodium-N,N,N',N'-tetra-(2-hydroxyethyl)-piperazinium silicate was formed using N,N'-(2-dihydroxyethyl)-piperazine. In this reaction, in the presence of the sodium silicate, ethylene oxide adds on to each nitrogen in the piperazine ring forming a quaternary ethanol compound. Thus, it is a derivative of tetra-ethanolammonium hydroxide in which two of the tetra-ethanolammonium hydroxy compounds are combined by the loss of $4CH_2OH$.

In this reaction, 70 parts of the piperazine compound was dissolved in 300 parts of water with 240 parts of E sodium silicate. A heavy coacervate formed, but the mixture was treated as usual at 25°–30° C. with 36 parts of ethylene oxide allowed to pass gradually into the reaction flask. In 6 minutes, the temperature had risen to 22.5° C. from 21° C., with an increase in coacevation. After 50 minutes, the temperature was 27° C. inside the flask and all of the ethylene oxide had been taken up. In 1 hour and 16 minutes, the temperature was 26.5° C. and the solution had become clear. In 5 hours, the temperature was 25° C. and the reaction was shut off and the flask left closed at room temperature overnight. There was no odor of ethylene oxide and crystals had formed on the bottom of the flask. On further refrigeration, a large number of crystals formed in a few hours. These were easily filtered and washed with ethanol and then washed twice with ether and dried in vacuo. The yield was about 7% based on the silica and 6.6% based on ethylene oxide or the piperazine. The mol ratio was $1Na_2O$:$2.2$ quaternary complex:$6.4SiO_2$:$19.3H_2O$. (The mole ratio for the oxide is the same as for the complex in this case). These crystals were elongated plates being strongly birefringent and having the refractive indices alpha=1.506, beta=1.512 and gamma=1.520. The crystals softened at about 140° C. and melted with decomposition at 110°–111° C. They were fairly insoluble in water and quite insoluble in the usual organic solvents.

This product contained an exceptionally low amount of $Na_2O$ as shown below and by continued washing with water, the $Na_2O$ content may be reduced below 1%.

|  | Before Washing | After Additional Washing (10×) |
|---|---|---|
| Percent $Na_2O$ | 4.50 | 0.09 |
| Percent Quaternary ion | 42.50 | 35.31 |
| Percent $SiO_2$ | 28.00 | 26.41 |
| Percent $H_2O$ | 25.36 | 37.54 |

I have also carried out essentially the same reaction starting with piperazine itself and forming ethanol groups by reaction with ethylene oxide. The final compound was the same.

EXAMPLE 10

Sodium-N,N,N'-tris-beta-hydroxyethyl-N'-tris-(beta-hydroxyethyl)-ethylammonium-piperazinium silicate was prepared using N-2-aminoethyl-piperazine. This again may be considered a derivative of tetraethanolammonium hydroxide in the same sense as the previous piperazine but in this case an additional tetraethanolammonium compound is combined with one of the ring nitrogens.

Fifty parts of the piperazine were dissolved in 300 parts of water and mixed with 240 parts of E sodium silicate. This formed a clear solution which was treated at about 25°–30° C. as usual with 53 parts of ethylene oxide. After 8 minutes it had risen to 28.5° C. with a coacervate forming but refluxing as the ethylene oxide was slowly added. After 18 minutes the temperature had risen to 33° C. showing a very strong exothermic reaction which had to be cooled with ice. More coacervate formed but no refluxing occurred. After 25 minutes the temperature was down to 25° C. and a heavy coacervate was present. At this time cooling with water was all that was required. After 1 hour the temperature was 28° C. and no refluxing was occurring. All the ethylene oxide had been added and the coacervate was dissolving. In 6 hours the temperature was 25.5° C. and the solution was clear. This clear solution was left in the refrigerator at 2° C. overnight without further concentration. Since no crystals formed, an additional 53 parts of ethylene oxide were added. No refluxing and no coacervation occurred and the ethylene oxide was added in 1 hour, 10 minutes. The reaction was left for 5 hours more, leaving a clear solution with a strong odor of ethylene oxide. No crystals formed when this solution cooled overnight. 173 Parts of water were distilled off and the concentrated solution was again cooled. At this time a fairly large amount of irregular crystals formed which were easily filtered and washed twice with ethanol, twice with ether, and dried in vacuo.

The yield was 13.1% based on the silica and 15.8% based on either the ethylene oxide or the piperazine. The crystals had a mol ratio of $1Na_2O:1.3$ quaternary complex ion:$4.7SiO_2$ $11.9H_2O(1Na_2O:1.9$ quaternary ammonium complex oxide:$4.7SiO_2:11.9H_2O$). They were diamond shaped in habit and had refractive indices of alpha=1.502, beta=1.512, gamma=1.520.

The crystals softened at 55° C. and melted at 64°–65° C. without decomposition. They dissolved readily in small amounts of water but not completely in larger amounts. They were insoluble in the usual organic solvents.

In the analysis of these crystals it is necessary to know which nitrogen compounds are titratable as $Na_2O$ is calculated from the determination of nitrogen and total titratable alkali. Thus only two of the three nitrogens in the N-2-amino-ethyl-piperazine can be titrated with HCl. In the other compounds all of the nitrogen was titratable.

UTILITY

The utility of the compounds produced in accordance with this invention is exactly as set forth in my parent U.S. Pat. No. 3,239,549 (column 21, line 21 to column 22, line 21) and said patent is hereby incorporated herein by reference.

In this invention the ratio of the components is obviously controlled by the relationships established for X, Y and Z in the general formula.

Since results analogous to those indicated in the foregoing examples are obtained with other equivalent reactants, it is not intended to limit the invention to the details of the examples but only broadly as defined in the following claims.

What is claimed is:

1. A process for preparing quaternary ammonium silicates which comprises reacting an alkylene oxide, a heterocyclic amine compound selected from the group consisting of morpholine, piperazine compounds and pyrrolidine compounds; and an alkali metal silicate in an aqueous system, crystallizing and recovering the crystallized product.

2. The method according to claim 1 wherein said heterocyclic amine is morpholine.

3. The method according to claim 1 wherein said heterocyclic amine is a piperazine compound.

4. The process of claim 1 wherein the alkylene oxide is ethylene oxide.

* * * * *